(12) United States Patent
Ali

(10) Patent No.: US 6,500,992 B1
(45) Date of Patent: Dec. 31, 2002

(54) SYNTHESIS OF METHYL TERTIARY BUTYL ETHER FROM METHANOL AND ISOBUTENE USING ALUMINUM-FLUORIDE-MODIFIED ZEOLITE CATALYSTS

(75) Inventor: Mohammad Ashraf Ali, Dhahran (SA)

(73) Assignee: King Fahd University of Petroleum & Minerals, Dhahran (SA)

( * ) Notice: Subject to any disclaimer, the term of this patent is extended or adjusted under 35 U.S.C. 154(b) by 0 days.

(21) Appl. No.: 09/708,545

(22) Filed: Nov. 9, 2000

(51) Int. Cl.$^7$ .............................................. C07C 41/06
(52) U.S. Cl. ........................................ 568/697; 502/64
(58) Field of Search ............................. 568/697; 502/64

(56) References Cited

U.S. PATENT DOCUMENTS

| | | | |
|---|---|---|---|
| 4,182,913 A | | 1/1980 | Takezono et al. |
| 4,530,756 A | * | 7/1985 | Chang et al. ............ 208/111.15 |
| 4,564,719 A | * | 1/1986 | Chang et al. ................ 585/408 |
| 4,605,787 A | * | 8/1986 | Chu et al. .................... 568/697 |
| 5,157,162 A | | 10/1992 | Knifton |
| 5,220,078 A | | 6/1993 | Knifton et al. |
| 5,300,697 A | | 4/1994 | Knifton et al. |
| 5,783,321 A | * | 7/1998 | Verduijn et al. ............. 423/702 |

FOREIGN PATENT DOCUMENTS

| | | | | |
|---|---|---|---|---|
| JP | 360231793 A | * | 11/1985 | ............ C10G/3/00 |

OTHER PUBLICATIONS

Davenport, Robert, E., Gasoline Octane Improvers. Chemical Economics Handbook, CEH Marketing Report, 1986, p. 543, Standard Research Institute, SRI International, Minlo Park, California.

Chu, P. and Kuhl, H., Preparation of methyl tertiary butyl ether (MTBE) over zeolite catalysts. Industrial and Engineering Chemistry Research, 1987, vol. 26, 365–369.

Izquierdo, J.F., Cunill, F., Vila, M., Tejero, J. and Iborra, M. Equilibrium constants fro methyl tertiary butyl ether liquid–phase synthesis. Journal of Chemical and Engineering Data, 1992, vol. 37, p. 339.

Brockwell, H.L., Sarathy, S.R. and Troffa, R. Synthesize Ethers. Hydrocarbon Processing, Sep. 1991, p. 133, vol. 70, No. 9.

Tejero, J. Molecular mechanism of MTBE synthesis on a sulfonic acid ion–exchange resin. Journal of Molecular Catalysis, 1987, vol. 42, p. 257.

Subraminium, C. and Bhatia, S. Liquid phase synthesis of MTBE4&talyzed by ion–exchange resin. Canadian Journal of Chemical Engineering, 1987, vol. 65, p. 613.

* cited by examiner

*Primary Examiner*—Rosalynd Keys
(74) *Attorney, Agent, or Firm*—Dennison, Schultz & Dougherty

(57) ABSTRACT

This invention concerns an improved and novel catalyst for preparing methyl tertiary butyl ether (MTBE). This invention is advantageous in that the reaction of methanol and isobutene takes place such that the catalysts exhibit levels of isobutene conversion as high as 98%, and the MTBE selectivity reaches as high as 98%. The improved catalysts comprises of a crystalline aluminosilicate zeolites, particularly MFI-type zeolites which has been treated with aluminum fluoride in the ratio 1 gram to 10 grams of zeolite with 0.5 gram to 5 grams of aluminum fluoride. A specific application of this improved and novel catalyst is reacting methanol and isobutene in a molar amount of about 0.1 mole to 10 moles of methanol per mole of isobutene, in the presence of said catalyst in a batch reactor, at about 70° C. to about 100° C., and a pressure of about 1 bar to 33 bar, to obtain MTBE product.

13 Claims, No Drawings

SYNTHESIS OF METHYL TERTIARY BUTYL ETHER FROM METHANOL AND ISOBUTENE USING ALUMINUM-FLUORIDE-MODIFIED ZEOLITE CATALYSTS

BACKGROUND OF THE INVENTION

It is well known that ethers may be prepared by reacting an alcohol with an olefin to form the desired product. The reaction mixture containing catalysts and/or condensing components may be separated and further treated to permit attainment of the desired product specification.

MTBE is being used as a blending component in high-octane gasoline, as the gasoline additives based on lead and manganese have been phased out. Currently, all commercial processes for the manufacture of MTBE are based upon the liquid phase reaction of isobutene and methanol catalyzed by cationic ion-exchange resin (see: Izquierdo, J. F., Cunill, F., Vila M., Tejero J. and Tborra M. Equilibrium constants for methyl tertiary butyl ether liquid-phase synthesis. Journal of Chemical and Engineering Data, 1992, vol. 37, p. 339.; Brockwell, H. L., Sarathy P. R. and Trotta R. Synthesize ethers. Hydrocarbon Processing, 1991, vol. 70, No. 9, p. 133.; Chemical Economics Handbook, Gasoline Octane Improvers. CEH Marketing Report, 1986, p. 543, Stanford Research Institute, SRI International, Menlo Park, Calif.). The isobutene is obtained by the fluid catalytic cracking process, from the isomerization of n-butene and dehydrogenation of isobutane. The methanol is produced from syngas (a mixture of carbon monoxide and hydrogen) obtained from the steam reforming of natural gas. The cationic ion-exchange resins used in MTBE synthesis normally have the sulfonic acid functionality (see: Tejero, J. Journal of Molecular Catalysis, 1987, vol. 42, p. 257; Subraminium and Bhatia, Canadian Journal of Chemical Engineering, 1987, vol. 65, p. 613).

These cationic ion-exchange resins are generally based on polystyrene-divinylbenzene backbone and have a very limited stability range with regard to operating temperatures, with temperatures above 100° C., normally leading to irreversible destruction of the resin and loss of catalytic activity. The catalyst life in commercial operation is about two years. The MTBE synthesis reaction is exothermic, yielding −37.7 kJ mol$^{-1}$ of energy.

The detrimental effects of instability of the resin catalyst used in the preparation of MTBE have been discussed in a patent by Takezono and Fujiwara [U.S. Pat. No. 4,182,913]. According to the findings of this study, at higher temperatures, a large quantity of acids is effused from the strongly acidic cation-exchange resin and the deterioration of the catalyst resin is accelerated. Even when the temperature is low, a small quantity of the strong acidic substance is effused into the reaction mixture. When such a reaction mixture containing the acid substance is fed into the succeeding step of unreacted gas separation, so as to separate the unreacted gas by distillation, the decomposition or reverse reaction of the main product is caused to occur, which reduces the yield. In addition, various portions of the apparatus are corroded by the strong acids released. In this reaction, diisobutene and tertiary butyl alcohol (TBA) are the by-products of dimerization of isobutene and reaction of water with isobutene respectively. The amount of diisobutene formed increases with rise in temperature [Chu and Kohl, Industrial and Engineering Chemistry Research, 1987, vol 26, p. 365]. TBA formation is insignificant as long as the feedstocks are thoroughly dried. According to LeChatlier's principle, the reaction equilibrium for MTBE formation is more favorable at lower temperatures, but reaction rate is decreased considerably. Thus current operation temperatures appear to be limited by three factors: (i). resin catalyst instability at temperature above 100° C.; (ii). poor selectivity due to dimerization above 100° C.; and (iii). equilibrium conversion limitation. It is also pointed out that the progress of the reaction over cationic ion-exchange resin is usually complicated by various adsorption and diffusion factors, by swelling phenomenon, and by the variable distribution of the components between the solution and cationic exchanger phase.

The zeolites have a porous structure and are represented by the following general formula;

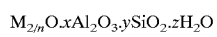

Where M is an alkali metal or alkaline earth metal cation or organic base cation, n is the valence of the cation and x and y are variables.

In U.S. Pat. No. 5,157,162 to Knifton there is disclosed a process for one-step synthesis of MTBE using tertiary butanol and methanol over a catalyst comprising fluorosulfonic acid modified montmorillonite clay at temperature of about 20° C. to about 250° C.

In U.S. Pat. No. 5,220,078, a process is disclosed for producing MTBE using tertiary butanol and methanol over a catalyst comprising of fluorophosphoric acid modified Y-type zeolite at temperature of about 20° C. to about 250° C.

U.S. Pat. No. 5,300,697 discloses a process for producing MTBE using tertiary butanol and methanol over a catalyst comprising of hydrogen fluoride modified Y-type zeolite at temperature of about 20° C. to about 250° C. All of these processes are limited by the fact that the conversion is low and the selectivity of the reaction for MTBE is quite small.

It would be a substantial improvement in the art if MTBE could be selectively synthesized from isobutene and methanol using a catalyst which allows for rapid conversion of isobutene. In our invention, aluminum fluoride-modified zeolite can be used as an improved and novel catalyst for the selective synthesis of MTBE from isobutene and methanol with high conversion. The accompanying examples demonstrate good yields of MTBE when using the modified zeolites of the instant invention for such a reaction.

SUMMARY OF THE INVENTION

In accordance with certain of its aspects, the novel method of this invention for preparing MTBE from methanol and isobutene comprises reacting methanol and isobutene in the presence of a catalyst comprising an aluminum fluoride-modified zeolite containing at least one metal from Group IIIA of the periodic table. Examples demonstrate particularly the effectiveness of an aluminum fluoride-modified MFI-type zeolite. MFI is the structure type code (allocated by the Structure Commission of the International Zeolite Association) to a number of zeolites having similar topology such as ZSM-5 and silicalite.

DESCRIPTION OF THE INVENTION

Preparation of the product using this invention may be carried out typically by reacting methanol and isobutene in the presence of an etherification catalyst. The etherification is carried out in one-step and the catalyst preferably comprises MFI-type zeolite modified hydrothermally with aluminum fluoride. This important reaction does not restrict the scope of the invention.

The reaction of isobutene and methanol can be represented by the following equation:

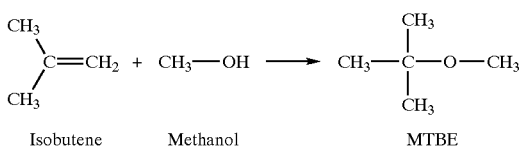

Isobutene    Methanol    MTBE

Generally the methanol and isobutene coreactants may be mixed in any proportion in order to generate the desired MTBE, but preferably the molar ratio of methanol to isobutene in the reaction mixture should be about 0.1 to 10. In order to achieve maximum selectivity to MTBE and optimum conversion per hour, an excess of methanol in the reaction mixture is desirable. The most preferred methanol-to-isobutene molar ratio is from 1:1 to 5:1.

The synthesis of MTBE according to the reaction given above can also be conducted where the isobutene and methanol reactants are mixed with other $C_4$ aliphatic and olefinic hydrocarbons such as isobutane, n-butane and n-butene.

The same etherification process may also be applied for the preparation of other alkyl tertiary ethers. For example, the said etherification process may be applied to the reaction of a $C_1$–$C_4$ primary alcohol such as methanol, ethanol, n-propanol and n-butanol with a $C_4$–$C_6$ tertiary olefin, such as for example, tertiary amyl olefin. Reaction of methanol with tertiary amyl olefin would then yield methyl tertiary amyl methyl ether (TAME). Similarly, reactions of ethanol with isobutene would then yield ethyl tertiary butyl ether (ETBE).

Good results were realized using certain crystalline aluminosilicate zeolites as catalysts for the reaction of isobutene and methanol to produce MTBE. The preferred zeolites are the MFI-type zeolites as well as zeolite beta and mordenite, modified hydrothermally with aluminum fluoride.

Zeolites possesses a number of catalytically-favorable properties such as well-defined crystalline structure, uniform pores, high surface area, good thermal stability, wide range of acidity and shape selectivity.

The unit cell of a MFI-type ZSM-5 zeolite contains 96 silicon or aluminum-centered oxygen tetrahedra which are linked through shared oxygen atoms. Because of the net negative charge on each of the aluminum-centered tetrahedra, each unit cell contains an equivalent number of charge balancing cations. These are exclusively sodium ions in zeolites in their synthesized form. MFI-type ZSM-5 zeolite in its hydrated and sodium form has the following general formula in which the number of aluminum atoms should be less than 27.

$$Na_n.Al_nSi_{96-n}.O_{192}.16H_2O$$

Particularly effective in the subject synthesis of MTBE are the synthetic MFI-type zeolites. Preferably said zeolites should be in a strongly acidic form whereby some or all of the cations (Group I or II, alkali or alkaline earth metals such as sodium, potassium, calcium or magnesium)) are exchanged by protons either through ammonium exchange followed by thermal stabilization (deammoniation or removal of ammonia) at elevated temperatures (for example 400° C. to 500° C.) or through mineral acid treatment, etc. The mineral acids may include hydrochloric acid, sulfuric acid or nitric acid.

The aluminum fluoride-modified zeolite is prepared by treating the said MFI-type zeolite with aluminum fluoride in the presence of distilled water. Preferably the aluminum fluoride is mixed with the distilled water in a sealed container and heated at elevated temperature before adding the zeolite to the said mixture of aluminum fluoride and distilled water.

In a further embodiment of the invention, the zeolite catalyst comprises 1 to 2 weight percent of the total reaction contents. In a further embodiment of the invention, the methanol comprises about 99 weight percent of methanol. In a further embodiment of the invention, the isobutene comprises about 98 weight percent of isobutene. In a further embodiment of the invention, methanol comprises about 41 weight percent of the reaction mixture. In a further embodiment of the invention, the isobutene comprises about 59 weight percent of the reaction mixture.

The said catalyst may be in the form of powders, pellets, granules, spheres, shapes and extrudates. The examples described herein demonstrate the advantages of using powder form.

The reaction may be carried out in either a stirred slurry reactor or in a fixed bed continuous flow reactor. The catalyst concentration should be sufficient to provide the desired catalytic effect.

Etherification can generally be conducted at temperatures from 40° C. to 150° C.; the preferred range is 40 to 100° C. The total operating pressure may be from 1 bar to 66 bar, or higher. The preferred pressure range is about 1 bar to 33 bar.

The examples which follow illustrate the synthesis of MTBE from methanol and isobutene using aluminum fluoride MFI-type zeolite particularly in the form of powder. The examples are a means of illustration and it is understood that the invention is not meant to be limited thereby.

Conversion of the isobutene (Isobutene, mole %) is estimated in the following examples using the equations:

$$\frac{\text{(Moles of Isobutene in the Feed)} - \text{(Moles of Isobutene in the Product)}}{\text{Moles of Isobutene in the Feed}} \times 100$$

Selectivity of MTBE (MTBE, mole %) is estimated from the following equation:

$$\frac{\text{Moles of MTBE in the Product}}{(\text{Moles of Isobutene in the Feed}) - (\text{Moles of Isobutene in the Product})} \times 100$$

It may be noted that
i. Comparing etherification data in Table I and Example 5, using the aluminum-fluoride-modified zeolite ZCIC-10, prepared by the method of Example 1, with the data of ZCIC-10 alone (Comparative Example A, Table V) it is seen that the isobutene conversion levels with aluminum-fluoride-modified zeolite of Example 5 occur at all operating temperatures, but particularly at 80° C. to 100° C. are at least three times higher than for ZCIC-10 alone.
ii. Comparing etherification data in Table II and Example 6, using the aluminum-fluoride-modified zeolite ZCIC-10, prepared by the method of Example 2, with data of ZCIC-10 alone (Comparative Example A, Table V) it is seen that the isobutene conversion levels with aluminum-fluoride-modified zeolite of Example 6 occur at all operating temperatures, but particularly at 80 to 100° C. are at least four times higher than for ZCIC-10 alone as well as higher than that of Example 5.
iii. Comparing etherification data in Table III and Example 7, using the aluminum-fluoride-modified zeolite ZCIC-10, prepared by the method of Example 3, with data of ZCIC-10 alone (Comparative Example A, Table V) it is seen that the isobutene conversion levels with aluminum-fluoride-modified zeolite of Example 7 occur at all operating temperatures, but particularly at 80 to 100° C. are significantly and measurably at least five times higher than for ZCIC-10 alone as well as higher than those of Example 5 (Table I) and 6 (Table II).
iv. Comparing etherification data in Table IV and Example 8, using the aluminum-fluoride-modified zeolite MZ-25, prepared by the method of Example 4, with data of MZ-25 alone (Comparative Example B, Table VI) it is seen that the isobutene conversion levels with aluminum-fluoride-modified zeolite of Example 8 occur at all operating temperatures, but particularly at 80 to 100° C. are significantly and measurably higher than for MZ-25 alone.
v. Comparing the etherification data in Table I and Example 5, using the aluminum-fluoride-modified zeolite ZCIC-10, prepared by the method of Example 1, with the data of aluminum-fluoride-modified zeolite MZ-25, prepared by the method of Example 4 and given in Table VI, it is seen that the isobutene conversion levels with aluminum-fluoride-modified zeolite of Example 5 occur at all operating temperatures are significantly and measurably higher than for aluminum-fluoride-modified zeolite MZ-25, prepared by the method of Example 4 and given in Table VI.
vi. Comparing the etherification data in Table V and Comparative Example A, using the ZCIC-10 zeolite, with the data of MZ-25 zeolite given in Table VI and Comparative Example B, it is seen that the isobutene conversion levels with ZCIC-10 zeolite given in Table V occur at all operating temperatures are significantly and measurably higher than for MZ-25 zeolite given in Table VI.

EXAMPLE 1

This example illustrates the preparation of an aluminum-fluoride-modified MFI-type zeolite. Aluminum fluoride, 2.2 grams as finely divided powder, was added in 200 ml of distilled water. The mixture was heated at about 100° C. to about 200° C. in a closed Teflon screw-capped 500 ml bottle for about 12 hours to about 18 hours. The mixture was cooled and was added with 10 grams of precalcined MEI-type zeolite (synthesized zeolite having a Si/Al molar ratio of 10, in powder form). The calcination of the zeolite was carried out at 400° C. to 500° C. programmed temperature in air having 100 ml/hour flow rate. The mixture was again heated at about 100° C. to about 200° C. for about 12 to about 18 hours and brought to ambient temperature. The resultant mixture was then filtered, washed several times with distilled water and dried in an air-circulated oven at 100° C. for 12 hours to about 18 hours. The recovered white powder was found to have the following elemental composition.

Fluorine, 1.39 wt %
Aluminum, 6.23 wt %
Silicon, 36.65 wt %
Si/Al molar ratio, 5.65
Si/F molar ratio, 17.84
Al/F molar ratio, 3.16

EXAMPLE 2

This example illustrates the preparation of an aluminum-fluoride-modified MFI-type zeolite. Aluminum fluoride, 4.4 grams as finely divided powder, was added in 200 ml of distilled water. The mixture was heated at about 100° C. to about 200° C. in a closed Teflon screw-capped 500 ml bottle for about 12 hours to about 18 hours. The mixture was cooled and was added with 10 grams of precalcined MFI-type zeolite (synthesized zeolite having a Si/Al molar ratio of 10, in powder form). The calcination of the zeolite was carried out at 400° C. to 500° C. programmed temperature in air having 100 ml/hour flow rate. The mixture was again heated at about 100° C. to about 200° C. for about 12 hours to about 18 hours and brought to ambient temperature. The resultant mixture was then filtered, washed several times with distilled water and dried in an air-circulated oven at 100° C. for 12 hours to about 18 hours. The recovered white powder was found to have the following elemental composition.

Fluorine, 1.70 wt %
Aluminum, 7.23 wt %
Silicon, 33.98 wt %
Si/Al molar ratio, 4.52
Si/F molar ratio, 12.56
Al/F molar ratio, 2.99

EXAMPLE 3

This example illustrates the preparation of an aluminum-fluoride-modified MFI-type zeolite. Aluminum fluoride, 6.6 grams as finely divided powder, was added in 200 ml of distilled water. The mixture was heated at about 100° C. to about 200° C. in a closed Teflon screw-capped 500 ml bottle for about 12 hours to about 18 hours. The mixture was cooled and was added with 10 grams of precalcined MFI-type zeolite (synthesized zeolite having a Si/Al molar ratio of 10, in powder form). The calcination of the zeolite was carried out at 400° C. to 500° C. programmed temperature in air having 100 ml/hour flow rate. The mixture was again heated at about 100° C. to about 200° C. for about 12 hours to about 18 hours and brought to ambient temperature. The resultant mixture was then filtered, washed several times with distilled water and dried in an air circulated oven at 100° C. for 12 hours to about 18 hours. The recovered white powder was found to have the following elemental composition.

Fluorine, 1.94 wt %
Aluminum, 7.73 wt %
Silicon, 33.74 wt %
Si/Al molar ratio, 4.21
Si/F molar ratio, 11.80
Al/F molar ratio, 2.80

EXAMPLE 4

This example illustrates the preparation of an aluminum-fluoride-modified MFI-type zeolite. Aluminum fluoride, 2.2 grams as finely divided powder, was added in 200 ml of distilled water. The mixture was heated at about 100° C. to about 200° C. in a closed Teflon screw-capped 500 ml bottle for about 12 hours to about 18 hours. The mixture was cooled and was added with 10 grams of precalcined MFI-type zeolite (Mobil MZ-25, powder form, having a Si/Al molar ratio of 25.50). The calcination of the zeolite was carried out at 400° C. to 500° C. programmed temperature in air having 100 ml/hour flow rate. The mixture was again heated at about 100° C. to about 200° C. for about 12 to about 18 hours and brought to ambient temperature. The resultant mixture was then filtered, washed several times with distilled water and dried in an air-circulated oven at 100° C. for 12 hours to about 18 hours. The recovered white powder was found to have the following elemental composition.

Fluorine, 0.47 wt %
Aluminum, 3.74 wt %
Silicon, 42.02 wt %
Si/Al molar ratio, 10.57
Si/F molar ratio, 59.22
Al/F molar ratio, 05.60

EXAMPLE 5

This example illustrates the production of MTBE from methanol and isobutene using aluminum-fluoride-modified MFI-type zeolite. The catalytic reactions were carried out in a batch reactor (manufactured by Parr Instrument Company, Moline, Ill., USA) using 1 gram of the said zeolite catalyst. This reactor consisted of reactor vessel, reactor head, heater, temperature controller, and temperature indicator. The reactor was equipped with all required fittings such as inlet valve, a gas release valve, a safety rupture disk, a pressure gauge, a stirrer driving system, oil circulating stainless steel coil and a thermowell for holding the thermocouple. The reactor vessel was a 500 ml stainless steel cylindrical pressure vessel. Vigorous mixing of the reactants, as well as uniform distribution of the catalyst or suspended solids, was achieved by impellers that were located on the stirring rod near the bottom of the vessel. The heater provided uniform heat distribution around the sides and the bottom of the vessel. The controller maintained the temperature of the autoclave in the range 0° C. to 400° C. with the use of a thermocouple.

The isobutene measuring and feed tube was made of thick QVF glass tube of 1.0 inch internal diameter and 18.0 inch in length. It was fitted at the top with a flange holding two valves, a vent valve and a valve connected to the inverted isobutene cylinder for allowing the isobutene in the tube. A second flange with a valve was attached at the bottom end for feeding isobutene to the preheater. This tube was calibrated to provide an accurate measure of the volume of isobutene fed into the preheater. The isobutene measuring and feed tube was connected to an inverted pressurized isobutene cylinder by metal tubings through which the liquid isobutene was drawn from the cylinder.

The reactor vessel was charged with 20.5 grams of methanol (0.64 mole) along with 1.0 gram of aluminum-fluoride-modified zeolite catalyst prepared by the method of Example 1 and was closed with the reactor head using split ring closures. A known volume of isobutene, 50 ml (0.53 mole), was taken into a isobutene measuring and feed tube. This constitutes a methanol-to-isobutene molar ratio of 1.2. Isobutene was charged into the reactor through the inlet valve of the reactor head assembly. The reactor was then pressurized with nitrogen to 13 bar to 17 bar. The reaction was carried out at 70° C. to 100° C. under constant stirring. The reaction time was 3 hours after the reactor achieved the desired temperature. The temperature of the reactor was maintained by circulating the oil in the stainless steel coils present in the reactor. At the end of the run, the reactor was allowed to cool and the contents were centrifuged to separate the fine particles of zeolite catalyst from the reaction product. The reaction products were analyzed using capillary column gas chromatography using a flame ionization detector. The reaction products were analyzed by mixing with a known amount of diisopropyl ether as an internal standard.

Typical analysis data for samples taken under these conditions are summarized in Table I. Performance at a series of other temperatures and methanol to isobutene molar ratios was determined using the same procedure. These results are summarized in Table I. Of note, isobutene conversion and MTBE selectivity are as follows:

| Sample | Reaction Temperature(° C.) | Isobutene Conversion % | MTBE Selectivity % |
| --- | --- | --- | --- |
| 1 | 80 | 57 | 98 |
| 2 | 100 | 74 | 95 |

EXAMPLE 6

This example illustrates the production of MTBE from methanol and isobutene using another aluminum-fluoride-modified MFI-type zeolite. Following the procedure of Example 5, the batch reactor was charged with 1.0 gram of zeolite catalyst of Example 2 and the performance was monitored over a series of temperature (70° C. to 100° C.) and methanol to isobutene molar ratios (1:1.1 to 2:1). These results are summarized in Table II. Calculated isobutene conversion and MTBE selectivity are as follows:

| Sample | Reaction Temperature(° C.) | Isobutene Conversion % | MTBE Selectivity % |
|---|---|---|---|
| 1 | 80 | 76 | 98 |
| 2 | 100 | 91 | 96 |

EXAMPLE 7

This example illustrates the production of MTBE from methanol and isobutene using another aluminum-fluoride-modified MFI-type zeolite. Following the procedure of Example 5, the batch reactor was charged with 1.0 gram of zeolite catalyst of Example 3 and the performance was monitored over a series of temperature (70° C. to 100° C.) and methanol to isobutene molar ratios (1:1.1 to 2:1). These results are summarized in Table III. Calculated isobutene conversion and MTBE selectivity are as follows:

| Sample | Reaction Temperature(° C.) | Isobutene Conversion % | MTBE Selectivity % |
|---|---|---|---|
| 1 | 80 | 79 | 98 |
| 2 | 100 | 98 | 97 |

EXAMPLE 8

This example illustrates the production of MTBE from methanol and isobutene using another aluminum-fluoride-modified MFI-type zeolite. Following the procedure of Example 5, the batch reactor was charged with 1.0 gram of zeolite catalyst Example 4 and the performance was monitored over a series of temperature (70° C. to 100° C.) and methanol to isobutene molar ratios (1:1.1 to 2:1). These results are summarized in Table III. Calculated isobutene conversion and MTBE selectivity are as

| Sample | Reaction Temperature(° C.) | Isobutene Conversion % | MTBE Selectivity % |
|---|---|---|---|
| 1 | 80 | 27 | 99 |
| 2 | 100 | 48 | 97 |

COMPARATIVE EXAMPLE A

This example illustrates the performance of an unmodified MFI-type zeolite in the production of MTBE from methanol and isobutene over a range of operating conditions. Using the equipment and procedures of Example 5, the batch reactor was charged with 1.0 gram of zeolite catalyst (ZCIC-10 synthesized zeolite having Si/Al molar ratio of 10, in powder form) and the performance was monitored over a series of temperature (70° C. to 100° C.) and methanol to isobutene molar ratios (1:1.1 to 2:1). These results are summarized in Table IV. Calculated isobutene conversion and MTBE selectivity at 80° C. and 100° C. are as follows:

| Sample | Reaction Temperature(° C.) | Isobutene Conversion % | MTBE Selectivity % |
|---|---|---|---|
| 1 | 80 | 19 | 80 |
| 2 | 100 | 35 | 79 |

COMPARATIVE EXAMPLE B

This example illustrates the performance of an unmodified MFI-type zeolite in the production of MTBE from methanol and isobutene over a range of operating conditions. Using the equipment and procedures of Example 5, the batch reactor was charged with 1.0 gram of zeolite catalyst (Mobil MZ-25, powder form, having weight percent composition of silicon 42.71, aluminum 1.61 and Si/Al molar ratio of 25.50) and the performance was monitored over a series of temperature (70° C. to 100° C.) and methanol to isobutene molar ratios (1:1.1 to 2:1). These results are summarized in Table V. Calculated isobutene conversion and MTBE selectivity at 80° C. and 100° C. are as follows:

| Sample | Reaction Temperature(° C.) | Isobutene Conversion % | MTBE Selectivity % |
|---|---|---|---|
| 1 | 80 | 16 | 94 |
| 2 | 100 | 30 | 91 |

TABLE I

| Example | Catalyst | MeOH/IB molar ratio | Reactants Charged (g) | Temperature ° C. | Product Composition, mole % | | | |
|---|---|---|---|---|---|---|---|---|
| | | | | | MTBE | TBA | IB | MeOH |
| 5 | Example 1 | 1.2 | 50 | 70 | 7.2 | 0.3 | 41.2 | 51.3 |
| | | | | 80 | 12.6 | 0.5 | 38.1 | 48.8 |
| | | | | 90 | 20.2 | 0.8 | 33.6 | 45.4 |
| | | | | 100 | 28.9 | 0.7 | 29.0 | 41.4 |

TABLE II

| Example | Catalyst | MeOH/IB molar ratio | Reactants Charged (g) | Temperature °C. | Product Composition, mole % | | | |
|---|---|---|---|---|---|---|---|---|
| | | | | | MTBE | TBA | IB | MeOH |
| 6 | Example 2 | 1.2 | 50 | 70 | 11.1 | 0.5 | 38.9 | 49.5 |
| | | | | 80 | 20.0 | 0.8 | 33.7 | 45.4 |
| | | | | 90 | 33.4 | 1.4 | 25.9 | 39.4 |
| | | | | 100 | 50.1 | 1.2 | 16.9 | 31.8 |

TABLE III

| Example | Catalyst | MeOH/IB molar ratio | Reactants Charged (g) | Temperature °C. | Product Composition, mole % | | | |
|---|---|---|---|---|---|---|---|---|
| | | | | | MTBE | TBA | IB | MeOH |
| 7 | Example 3 | 1.2 | 50 | 70 | 12.7 | 0.5 | 38.1 | 48.8 |
| | | | | 80 | 23.1 | 0.9 | 32.0 | 44.1 |
| | | | | 90 | 39.1 | 1.5 | 22.6 | 36.8 |
| | | | | 100 | 60.0 | 1.4 | 11.4 | 27.3 |

TABLE IV

| Example | Catalyst | MeOH/IB molar ratio | Reactants Charged (g) | Temperature °C. | Product Composition, mole % | | | |
|---|---|---|---|---|---|---|---|---|
| | | | | | MTBE | TBA | IB | MeOH |
| 8 | Example 4 | 1.2 | 50 | 70 | 3.8 | 0.1 | 43.3 | 52.8 |
| | | | | 80 | 6.5 | 0.1 | 41.8 | 51.6 |
| | | | | 90 | 10.0 | 0.2 | 39.8 | 50.0 |
| | | | | 100 | 13.8 | 0.2 | 37.8 | 48.3 |

TABLE V

| Example | Catalyst | MeOH/IB molar ratio | Reactants Charged (g) | Temperature °C. | Product Composition, mole % | | | |
|---|---|---|---|---|---|---|---|---|
| | | | | | MTBE | TBA | IB | MeOH |
| A | ZCIC-10 | 1.2 | 50 | 70 | 2.4 | 1.2 | 43.0 | 53.5 |
| | | | | 80 | 4.0 | 2.0 | 41.3 | 52.7 |
| | | | | 90 | 6.1 | 3.0 | 39.1 | 51.8 |
| | | | | 100 | 8.3 | 2.5 | 38.4 | 50.8 |

TABLE VI

| Example | Catalyst | MeOH/IB molar ratio | Reactants Charged (g) | Temperature °C. | Product Composition, mole % | | | |
|---|---|---|---|---|---|---|---|---|
| | | | | | MTBE | TBA | IB | MeOH |
| B | MZ-25 | 1.2 | 50 | 70 | 2.1 | 0.3 | 44.1 | 53.6 |
| | | | | 80 | 3.5 | 0.4 | 43.1 | 53.0 |
| | | | | 90 | 5.3 | 0.7 | 41.9 | 52.1 |
| | | | | 100 | 7.2 | 0.6 | 41.0 | 51.3 |

While the instant invention has been described by specific examples and embodiments, there is no intent to limit the inventive concept except as set forth in the following claims.

What is claimed is:

1. A process for the preparation of an alkyl tertiary-alkyl ether, comprising reacting an alcohol and an olefinic hydrocarbon at a temperature of about 40° C. to about 150° C. in the presence of an aluminum fluoride-modified zeolite catalyst having an pre-calcined silica/alumina ratio 10, and recovering the alkyl tertiary-alkyl ether.

2. A process according to claim 1 wherein the alcohol is methanol and the olefnic hydrocarbon is isobutene.

3. A process according to claim 1 wherein the zeolite catalyst comprises 1 to 2 weight percent of the total reaction contents.

4. A process according to claim 2 wherein the methanol comprises about 99 weight percent of methanol.

5. A process according to claim 2 wherein the isobutene comprises about 98 weight percent of isobutene.

6. A process according to claim 2 wherein methanol comprises about 41 weight percent of the reaction mixture.

7. A process according to claim 2 wherein the isobutene comprises about 59 weight percent of the reaction mixture.

8. A process according to claim 2 wherein the methanol and isobutene are present in a molar ratio of one mole of isobutene to 0.1 mole to 10 moles of methanol.

9. A process according to claim 1 in which the alkyl tertiary-alkyl ether is methyl tertiary butyl ether.

10. A process according to claim 1 wherein the alkyl tertiary-alkyl ether comprises mainly methyl tertiary butyl ether rich mixture containing unreacted isobutene and methanol.

11. A process according to claim 1 wherein the said aluminum-fluoride-modified zeolite catalyst is in the hydrogen form of zeolite.

12. A process according to claim 1 wherein the catalyst is a crystalline aluminosilicate MFI-type zeolite modified with aluminum fluoride salt.

13. A process according to claim 1 wherein the reaction is carried out at a pressure of about 1 bar to 33 bar.

* * * * *